United States Patent
Kim et al.

(10) Patent No.: US 11,650,008 B2
(45) Date of Patent: May 16, 2023

(54) METHOD FOR VAPORIZING LIQUID PROPANE AND VAPORIZING APPARATUS USED THEREFOR

(71) Applicant: LG CHEM, LTD., Seoul (KR)

(72) Inventors: Tae Woo Kim, Daejeon (KR); Sung Kyu Lee, Daejeon (KR); Inseop Kim, Daejeon (KR); Joon Ho Shin, Daejeon (KR)

(73) Assignee: LG CHEM, LTD., Seoul (KR)

( * ) Notice: Subject to any disclaimer, the term of this patent is extended or adjusted under 35 U.S.C. 154(b) by 517 days.

(21) Appl. No.: 16/635,102

(22) PCT Filed: Sep. 5, 2018

(86) PCT No.: PCT/KR2018/010327
§ 371 (c)(1),
(2) Date: Jan. 29, 2020

(87) PCT Pub. No.: WO2019/103290
PCT Pub. Date: May 31, 2019

(65) Prior Publication Data
US 2021/0095920 A1   Apr. 1, 2021

(30) Foreign Application Priority Data

Nov. 24, 2017 (KR) .......................... 10-2017-0158631
Aug. 30, 2018 (KR) .......................... 10-2018-0102507

(51) Int. Cl.
*C10G 9/00* (2006.01)
*F17C 7/04* (2006.01)
(Continued)

(52) U.S. Cl.
CPC .............. *F25J 3/0219* (2013.01); *C07C 4/04* (2013.01); *C10G 9/00* (2013.01); *F17C 7/04* (2013.01);
(Continued)

(58) Field of Classification Search
None
See application file for complete search history.

(56) References Cited

U.S. PATENT DOCUMENTS 3,323,315 A    6/1967   Carr
4,384,160 A    5/1983   Skraba
(Continued)

FOREIGN PATENT DOCUMENTS

CN    201503189 U    6/2010
CN    105545391 A    5/2016
(Continued)

OTHER PUBLICATIONS

Machine translation JP 2002-349795. Retrieved May 10, 2022 (Year: 2022).*

*Primary Examiner* — Philip Y Louie
*Assistant Examiner* — Alyssa L Cepluch
(74) *Attorney, Agent, or Firm* — Dentons US LLP

(57) ABSTRACT

A method for vaporizing liquid propane to be supplied as a raw material to a naphtha cracking ractor. The method comprises: decompressing liquid propane to lower a vaporization point and vaporize at least a portion of the liquid propane; utilizing vaporization heat, generated during vaporization of the portion of liquid propane, as a refrigerant; compressing the vaporized propane gas to increase pressure of the propane gas and produce compressed propane gas; and preheating the compressed propane gas. By using this method, it is possible to reduce pressure of liquid propane to a significantly lower pressure than the related art method so that all the vaporization latent heat or vaporization heat included in liquid propane may be utilized as a refrigerant, while also reducing heat energy consumed in a preheat process before it is supplied to the naphtha cracking reactor.

9 Claims, 2 Drawing Sheets

(51) Int. Cl.
  *C07C 4/04*    (2006.01)
  *F25J 3/02*    (2006.01)
(52) U.S. Cl.
  CPC .... *F25J 3/0238* (2013.01); *C10G 2300/1044* (2013.01); *F17C 2221/035* (2013.01); *F25J 2210/12* (2013.01); *F25J 2210/62* (2013.01); *F25J 2215/64* (2013.01)

(56) References Cited

U.S. PATENT DOCUMENTS

| | | |
|---|---|---|
| 5,499,615 A | 3/1996 | Lawrence et al. |
| 2015/0047391 A1 | 2/2015 | Suffridge et al. |

FOREIGN PATENT DOCUMENTS

| | | | |
|---|---|---|---|
| CN | 106949375 A | | 7/2017 |
| JP | 57-185226 A | | 11/1982 |
| JP | 2001-81484 A | | 3/2001 |
| JP | 2002-349795 A | | 12/2002 |
| JP | 2002349795 A | * | 12/2002 |
| JP | 2004-67992 A | | 3/2004 |
| JP | 4596620 B2 | | 10/2010 |
| KR | 1987-0001968 B1 | | 10/1987 |
| KR | 0131579 B1 | | 12/1997 |
| KR | 10-2005-0056941 A | | 6/2005 |
| KR | 10-2007-0066560 A | | 6/2007 |
| KR | 10-2009-0100121 A | | 9/2009 |
| KR | 10-2010-0015102 A | | 2/2010 |
| KR | 10-2015-0114196 A | | 10/2015 |
| KR | 10-2017-0049663 A | | 5/2017 |

* cited by examiner

FIG. 1 – RELATED ART
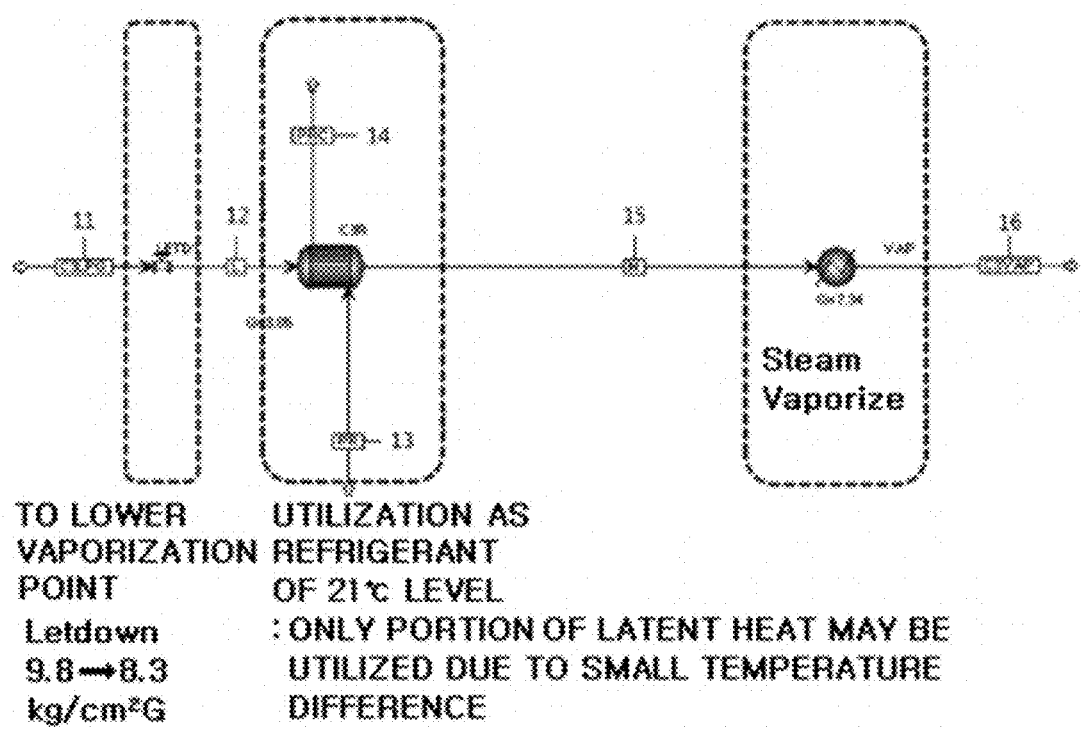
FIG. 2
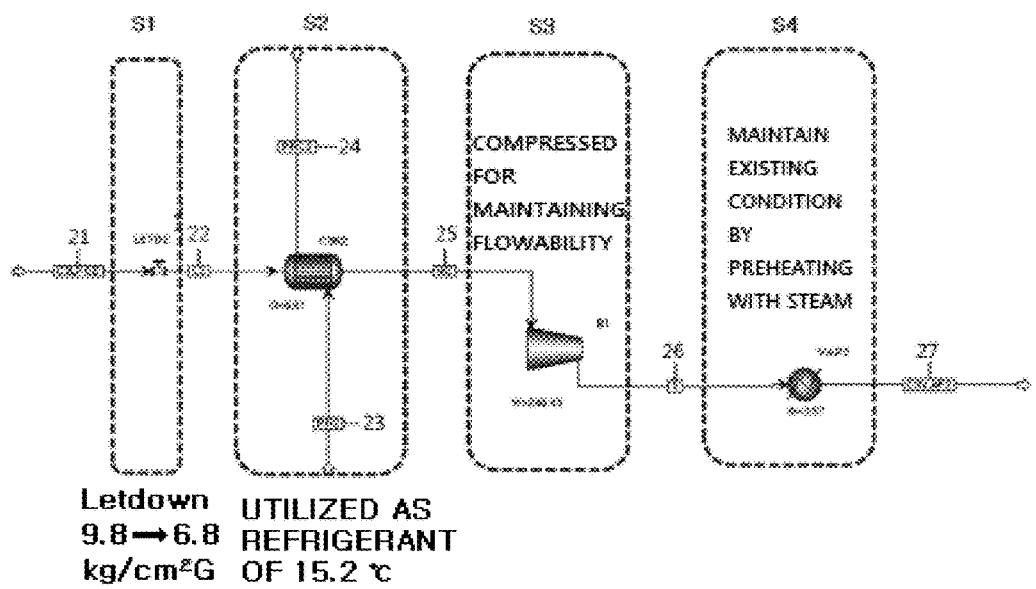

METHOD FOR VAPORIZING LIQUID PROPANE AND VAPORIZING APPARATUS USED THEREFOR

CROSS-REFERENCE TO RELATED APPLICATIONS

This application is a National Stage entry of International Application No. PCT/KR2018/010327 filed on Sep. 5, 2018, and claims priority under 35 U.S.C. § 119 to Korean Patent Application No. 10-2017-0158631, filed on Nov. 24, 2017, and Korean Patent Application No. 10-2018-0102507, filed on Aug. 30, 2018, whose entire disclosures are herein incorporated by reference.

TECHNICAL FIELD

The present invention relates to a process for vaporizing and supplying liquid propane when it is used as a raw material for a naphtha cracker, and more particularly, to a method for more efficiently using vaporization heat generated during a vaporization process of liquid propane.

BACKGROUND ART

Naphtha crackers mainly produce naphtha byproducts such as ethylene, propylene, butadiene, BTX, and the like, by injecting naphtha with steam at high temperatures and then cutting carbon rings by heating to 1000° C. or higher. Due to the emergence of shale gas and price reduction of materials, i.e., ethane, propane, butane, and the like, which may be used as raw materials for producing ethylene, instead of naphtha, existing naphtha crackers commonly use a mix of these gases as raw materials and new facilities are designed to use these gases as raw materials in many cases.

Many consumers use naphtha crackers for low-temperature refrigerants for refining products. For example, an ethylene refining column consumes 40 G cal/hr of a refrigerant having −40° C., and a considerable amount of refrigerant is also required for a deethanizer column or a demethanizer column.

Meanwhile, gas materials such as propane, or the like, are kept in a liquid state and vaporized before being injected into a reactor, and here, a heat source such as steam or hot water is consumed. If the gas materials are utilized by heat-exchanging with the refrigerant consumers, both the heat sources and the refrigerants may be saved.

DISCLOSURE

Technical Problem

An object of the present invention is to provide a method for efficiently utilizing vaporization heat of liquid propane as a refrigerant when liquid propane is used as a raw material for naphtha cracking.

Another object of the present invention is to provide a vaporizer for vaporizing liquid propane used in the above method.

Technical Solution

In one general aspect, a method for vaporizing liquid propane which is to be injected as a raw material into a naphatha cracking reactor, includes:

S1) decompressing liquid propane to lower a vaporization point to vaporize at least a portion of the liquid propane;

S2) utilizing vaporization heat based on vaporization of the liquid propane, as a refrigerant;

S3) compressing the vaporized propane gas to increase a pressure of a gas; and

S4) preheating the compressed propane gas.

According to an aspect, in the decompression step S1), the pressure of the liquid propane may be reduced to 7 $kg/cm^2$ gauge or less, and in step S2), the vaporization heat based on the liquid propane may be used as a refrigerant having a temperature less than 20° C.

According to another aspect, in the decompression step S1), the pressure of the liquid propane may be reduced to 1 $kg/cm^2$ gauge or less, and in step S2), the vaporization heat based on the liquid propane may be used as a refrigerant having a temperature of −20° C. or less.

According to an aspect, a utilization amount of the refrigerant using the vaporization heat based on decompression of the liquid propane may be 0.05 Gcal/hr or more per 1 ton/hr of propane.

According to an aspect, in step S3), the propane gas may be compressed at a pressure of 7 $kg/cm^2$ gauge or more.

According to an aspect, in step S3), a shaft work for compressing the propane gas may be 1 kW to 50 kW per 1 ton/hr of propane.

According to an aspect, in step S4), a consumption amount of steam consumed for preheating the compressed propane gas may be 0.08 G cal/hr or less per 1 ton/hr of propane.

According to an aspect, the propane gas compressed in step S3) may be preheated at a temperature of 100° C. or more in step S4).

In another general aspect, a vaporizer for vaporizing liquid propane which is to be injected into a naphtha cracking reactor includes:

a decompressing device decompressing liquid propane to lower a vaporization point to vaporize at least a portion of the liquid propane;

a heat-exchanger utilizing vaporization heat based on vaporization of the liquid propane;

a compressor compressing the decompressed liquid propane gas; and a preheating device preheating the compressed gas.

According to an aspect, the preheating device may use steam as a heat source.

Advantageous Effects

According to the present invention, since the process of vaporizing liquid propane and supplying the same as a raw material to the naphtha cracking reactor includes the process of compressing a decompressed propane gas, flowability of the decompressed propane gas may be maintained and decompression pressure may be significantly lowered, and thus, vaporization heat may be more effectively used. In addition, heat energy consumed for additional vaporization and preheating of the propane gas during preheating at a previous stage of supplying a raw material to the naphtha cracking reactor may also be reduced.

DESCRIPTION OF DRAWINGS

FIG. 1 is a schematic view illustrating a process of vaporizing liquid propane used in the related art.

FIGS. 2 and 3 are schematic views illustrating a process of vaporizing liquid propane according to various embodiments of the present invention.

BEST MODE

Figure 3:
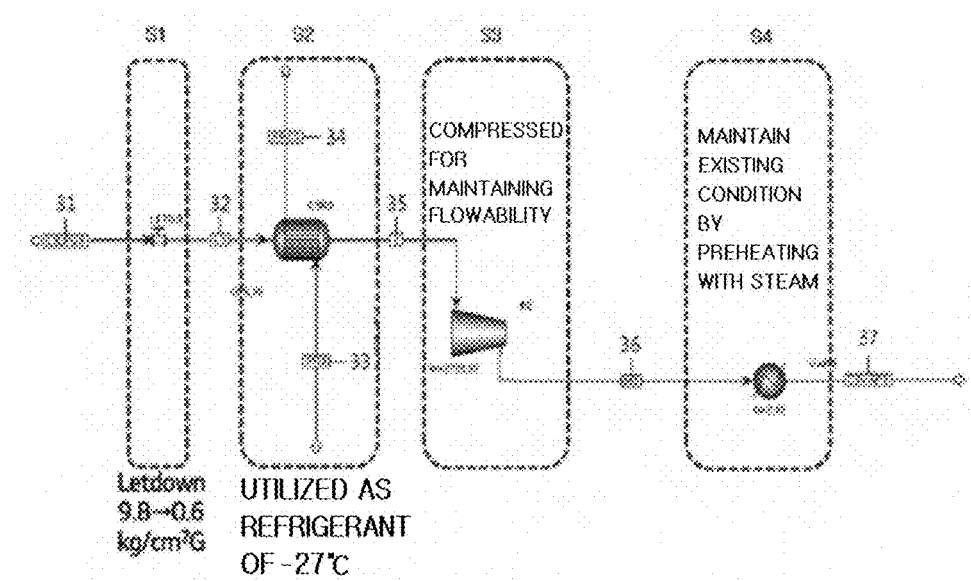

The present invention may be modified variably and may have various embodiments, particular examples of which will be illustrated in drawings and described in detail. However, it is to be understood that the present disclosure is not limited to a specific disclosed form, but includes all modifications, equivalents, and substitutions without departing from the scope and spirit of the present disclosure. In describing embodiments of the present invention, when it is determined that a detailed description of known techniques associated with the present disclosure unnecessarily obscures the gist of the present disclosure, the detailed description thereof will be omitted.

When transferred and stored, liquid propane (C3 LPG) is supplied in a liquid state, and thus, liquid propane is lead in through a vaporization process before entering a naphtha cracking reactor.

Here, a portion of liquid propane may be utilized as a refrigerant because a vaporization temperature thereof is low. However, in the existing process as illustrated in FIG. 1, pressure cannot be lowered sufficiently to maintain flowability allowing liquid propane to be introduced into the reactor. In the existing process, liquid propane is used by lowering a vaporization point thereof to a level to decompress pressure of liquid propane (C3LPG) from 9.8 to 8.3 $kg/cm^2$ gauge. In this case, the degree of decompression is so small that it may be utilized as a refrigerant at about 21° C., and since the temperature is not significantly different from room temperature, than the value as a refrigerant is low. Therefore, the refrigerant may not be sufficiently utilized and a considerable portion thereof may be additionally vaporized using a heat source such as steam or hot water.

In order to solve the related art problem, the present invention provides a method for vaporizing liquid propane including:

S1) decompressing liquid propane to lower a vaporization point to vaporize at least a portion of the liquid propane;

S2) utilizing vaporization heat based on vaporization of the liquid propane, as a refrigerant;

S3) compressing the vaporized propane gas to increase pressure of a gas; and

S4) preheating the compressed propane gas.

That is, in order to solve the problem that vaporization heat generated during a vaporization process of liquid propane is not effectively used because pressure is not sufficiently lowered during the vaporization process, flowability of decompressed gas is adjusted by providing a compression process using a compressor after the decompression process. Accordingly, decompression may be performed to sufficiently lower a vaporization point of liquid propane during the decompression process, whereby a utilization amount as a refrigerant may be significantly enhanced using vaporization heat of liquid propane.

Also, in addition to receiving heat required for vaporization from the outside during the process in which the heat is used as a refrigerant, since a temperature of the propane gas is increased through the compression process, a consumption amount of heat energy consumed during a preheating process before being supplied to the naphtha cracking reactor may also be significantly reduced.

FIGS. 2 and 3 illustrate various embodiments according to the present invention.

According to an embodiment, pressure of liquid propane may be reduced to 7 $kg/cm^2$ gauge or less in the decompression step, and the magnitude of the decompressed pressure may be adjusted according to conditions such as a cooling temperature, or the like, using the vaporization heat.

The refrigerant using the vaporization heat generated during the decompression process may be used as a refrigerant having a temperature less than 20° C., may be used as a refrigerant for cooling to obtain a difference in temperature of 10° C. or more than room temperature, for example, and may also be used as a refrigerant for a cooling temperature of 0° C. or less depending on the degree of decompression.

For example, according to the process of FIG. 2, during the decompression step S1), pressure of liquid propane may be reduced to 7 $kg/cm^2$ gauge or less, e.g., 5 $kg/cm^2$ gauge to 6.8 $kg/cm^2$ gauge, and in step S2), the vaporization heat based on liquid propane may be used as a refrigerant having a temperature less than 20° C., e.g., a refrigerant having a temperature ranging from 10 to 18° C.

Also, according to the process of FIG. 3, during the decompression step S1), pressure of liquid propane may be reduced to 1 $kg/cm^2$ gauge or less, e.g., 0.3 $kg/cm^2$ gauge to 0.8 $kg/cm^2$ gauge, and in step S2), the vaporization heat based on liquid propane may be used as a refrigerant having a temperature of −20° C. or less, e.g., a refrigerant having a temperature ranging from −25° C. to −30° C.

For example, the vaporization heat may be used as a refrigerant for prechilling an extract of a reactor such as an ethylene rectification column, a demethanizer column, a deethanizer column or a raw material of a distillation column, or in a condenser of a distillation column through a heat exchanger.

According to an embodiment, a utilization amount of the refrigerant using vaporization heat generated during the decompression process may be 0.05 Gcal/hr or more per 1 ton/hr of propane, preferably, 0.07 Gcal/hr or more per 1 ton/hr of propane, and more preferably, 0.08 Gcal/hr or more per 1 ton/hr of propane.

Also, according to an embodiment, the decompressed propane gas may be compressed using a compressor to maintain flowability thereof. Here, in order to compress the propane gas using the compressor, a shaft work of 1 kW to 50 kW per 1 ton/hr of propane may be used, and preferably, a shaft work of 3 kW to 35 kW per 1 ton/hr of propane may be used.

Also, through the compression process, the propane gas may be compressed to a pressure of 7 to 8 $kg/cm^2$ gauge, or may be compressed to a pressure of 4 to 10 $kg/cm^2$ gauge according to the pressure in a rear stage process, and the temperature may be increased by about 8° C. to 100° C.

The propane gas compressed under the above conditions may be decompressed to a significantly low pressure so that the liquid propane may be sufficiently vaporized, and the temperature is increased through the compression process to reduce a consumption amount of heat energy used in the preheat process.

According to an embodiment, the compressed propane gas may be introduced into the naphtha cracking reactor through a preheat process. Here, a consumption amount of heat energy of the heat source consumed for preheating may be 0.05 Gcal/hr or less per 1 ton/hr of propane. In the related art, the propane gas is not decompressed to a sufficiently low pressure, so the liquid propane must be additionally vaporized through a heat source, causing a consumption amount of heat energy to be increased to 0.09 Gcal/hr or more per 1 ton/hr of propane. In contrast, in the present invention, the propane gas may be decompressed to a significantly low pressure, as compared with the existing decompression process, so the liquid propane may be sufficiently vaporized, and since the temperature is increased through the compression process, a consumption amount of heat energy used for the preheat process may be reduced.

The present invention also provides a vaporizer for using the vaporization method.

More specifically, according to the present invention, a vaporizer for vaporizing liquid propane which is to be injected into a naphtha cracking reactor includes: a decompression device decompressing liquid propane to lower a vaporization point to vaporize at least a portion of the liquid propane; a heat-exchanger utilizing vaporization heat based on vaporization of the liquid propane; a compressor compressing the decompressed propane gas; and a preheat device preheating the compressed gas.

According to an embodiment, the preheat device may use steam, hot water, electric heater, or the like, as a heat source but is not limited thereto, and preferably, steam may be used.

Hereinafter, embodiments of the present invention will be described in detail so that those skilled in the art may easily carry out the present invention. However, the present invention may be embodied in many different forms and is not limited to the embodiments described herein.

COMPARATIVE EXAMPLE 1

Propane was vaporized using the propane vaporization process illustrated in FIG. 1.

A temperature, pressure and flow rate in each unit of the process illustrated in FIG. 1 are illustrated in Table 1. In the following, codes denote as follows.

C3LPG: Liquid propane
C3VAP: Gaseous propane
PRC: Propylene refrigerant compressor
PR: Propylene refrigerant
L, M, 1, 2, etc. are line codes.

TABLE 1

| Classification | C3LPG (11) | L (12) | PR (13) | PRC (14) | M (15) | C3VAP (16) |
|---|---|---|---|---|---|---|
| Temperature (° C.) | 17.9 | 17.9 | 29.0 | 24.1 | 21.1 | 120.0 |
| Pressure (kg/cm$^2$ gauge) | 9.80 | 8.30 | 12.80 | 12.60 | 7.80 | 7.80 |
| Propane flow rate (kg/hr) | 78659 | 78659 | 913300 | 913300 | 78659 | 78659 |
| Gas mass fraction | 0.000 | 0.000 | 0.000 | 0.000 | 0.441 | 1.000 |

EXAMPLE 1

Liquid propane was vaporized using the propane vaporization process illustrated in FIG. 2.

Vaporization heat based on decompression was utilized as a refrigerant of 15.2° C., and a temperature, pressure, a propane flow rate, and the like, used in the vaporization process are illustrated in Table 2.

TABLE 2

| Classification | C3LPG2 (21) | L2 (22) | PR2 (23) | PRC2 (24) | M2 (25) | 1 (26) | C3VAP2 (27) |
|---|---|---|---|---|---|---|---|
| Temperature (° C.) | 17.9 | 16.1 | 29.0 | 18.2 | 15.2 | 24.1 | 120.0 |
| Pressure (kg/cm$^2$ gauge) | 9.80 | 6.80 | 12.80 | 12.60 | 6.30 | 7.80 | 7.80 |
| Propane flow rate (kg/hr) | 78659 | 78659 | 913300 | 913300 | 78659 | 78659 | 78659 |
| Gas mass fraction | 0.000 | 0.014 | 0.000 | 0.000 | 1.000 | 1.000 | 1.000 |

EXAMPLE 2

Liquid propane was vaporized using the propane vaporization process illustrated in FIG. 3.

Vaporization heat based on decompression was utilized as a refrigerant of −27° C., and a temperature, pressure, a propane flow rate, and the like, used in the vaporization process are illustrated in Table 3.

TABLE 3

| Classification | C3LPG3 (31) | L3 (32) | PR3 (33) | PRC3 (34) | 2 (35) | M3 (36) | C3VAP3 (37) |
|---|---|---|---|---|---|---|---|
| Temperature (° C.) | 17.9 | −31.0 | −20.0 | −23.9 | −26.9 | 56.8 | 120.0 |
| Pressure (kg/cm$^2$ gauge) | 9.80 | 0.60 | 2.11 | 1.70 | 0.20 | 7.80 | 7.80 |

TABLE 3-continued

| Classification | C3LPG3 (31) | L3 (32) | PR3 (33) | PRC3 (34) | 2 (35) | M3 (36) | C3VAP3 (37) |
|---|---|---|---|---|---|---|---|
| Propane flow rate (kg/hr) | 78659 | 78659 | 100000 | 100000 | 78659 | 78659 | 78659 |
| Gas mass fraction | 0.000 | 0.299 | 1.000 | 0.436 | 1.000 | 1.000 | 1.000 |

Table 4 shows comparison between a refrigerant temperature, a utilization amount of refrigerant, a consumption amount of steam, and compressor shaft work according to the processes of Comparative Example 1 and Examples 1 and 2.

TABLE 4

| | decompression pressure (kg/cm² gauge) | Refrigerant temperature (° C.) | Flow rate of propane (ton/hr) | Utilization amount of refrigerant (Gcal/hr) | | Heat amount of Preheat (Gcal/hr) | | Compressor shaft work (kW) | |
|---|---|---|---|---|---|---|---|---|---|
| | | | | total | Per 1 ton of propane | total | Per 1 ton of propane | total | Per 1 ton of propane |
| Comparative Example 1 | 8.3 | 21 | 78.66 | 3.05 | 0.039 | 7.34 | 0.093 | — | |
| Example 1 | 6.8 | 15.2 | 78.66 | 6.61 | 0.084 | 3.57 | 0.045 | 246.43 | 3.13 |
| Example 2 | 0.6 | −27 | 78.66 | 5.7 | 0.072 | 2.42 | 0.031 | 2725.07 | 34.64 |

As can be seen from the results of Table 4, according to the present invention, since flowability of the decompressed propane gas is maintained using a compression unit such as a compressor in the compression step (S3), decompression is sufficiently performed in the decompression step (S1). Therefore, the vaporization point may be significantly lowered in vaporization through the decompression process of liquid propane, thus significantly enhancing utilization of vaporization heat.

In addition, since consumption of heat energy for additional vaporization is reduced in the preheat step (S4) by steam, a consumption amount of steam is also reduced by half or more as compared with the existing method (Comparative Example 1).

While the present invention has been particularly shown and described with reference to specific embodiments thereof, those skilled in the art will appreciate that such specific embodiments are merely preferred embodiments and the scope of the present invention is not limited thereto. Therefore, the substantial scope of the present invention will be defined by the appended claims and their equivalents.

The invention claimed is:

1. A method for vaporizing liquid propane which is to be injected as a raw material into a naphatha cracking reactor, the method for vaporizing liquid propane comprising:
    S1) decompressing liquid propane to lower an initial vaporization point and vaporize at least a portion of the liquid propane to produce propane gas;
    S2) utilizing vaporization heat generated during vaporization of the portion of liquid propane as a refrigerant;
    S3) compressing the propane gas to increase pressure of the propane gas and produce compressed propane gas; and
    S4) preheating the compressed propane gas to produce preheated propane gas and introducing the preheated propane gas into the naphtha cracking reactor.

2. The method of claim 1, wherein,
    in the decompression step S1), the pressure of the liquid propane is reduced to 7 kg/cm' gauge or less, and in step S2), the vaporization heat generated during vaporization of the portion of the liquid propane is used as a refrigerant having a temperature of less than 20° C.

3. The method of claim 1, wherein,
    in the decompression step S1), the pressure of the liquid propane is reduced to 1 kg/cm' gauge or less, and in step S2), the vaporization heat generated during vaporization of the portion of the liquid propane is used as a refrigerant having a temperature of −20° C. or less.

4. The method of claim 1, wherein,
    in step S2), a utilization amount of the refrigerant using the vaporization heat generated during vaporization of the portion of the liquid propane is 0.05 Gcal/hr or more per 1 ton/hr of propane.

5. The method of claim 1, wherein,
    in step S3), the propane gas is compressed at a pressure of 7 kg/cm² gauge or more.

6. The method of claim 1, wherein,
    in step S3), a shaft work for compressing the propane gas is 1 kW to 50 kW per 1 ton/hr of propane.

7. The method of claim 1, wherein,
    in step S4), a consumption amount of steam consumed for preheating the compressed propane gas is 0.08 Gcal/hr or less per 1 ton/hr of propane.

8. The method of claim 1, wherein,
    the propane gas compressed in step S3) is preheated at a temperature of 100° C. or more in step S4).

9. The method of claim 1, wherein the initial vaporization point of the liquid propane is 9.8 kg/cm² gauge.

* * * * *